US009752139B2

United States Patent
Becker et al.

(10) Patent No.: US 9,752,139 B2
(45) Date of Patent: Sep. 5, 2017

(54) MAGNETIC THREE-DIMENSIONAL CELL CULTURE APPARATUS AND METHOD

(71) Applicant: University of South Florida, Tampa, FL (US)

(72) Inventors: Jeanne L. Becker, Tampa, FL (US); Susan B. Coffin, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/096,791

(22) Filed: Dec. 4, 2013

(65) Prior Publication Data

US 2014/0087440 A1  Mar. 27, 2014

Related U.S. Application Data

(60) Division of application No. 12/330,071, filed on Dec. 8, 2008, now abandoned, which is a continuation- (Continued)

(51) Int. Cl.

| C12M 1/00 | (2006.01) |
|---|---|
| C12M 3/00 | (2006.01) |
| C12N 13/00 | (2006.01) |
| B82Y 25/00 | (2011.01) |
| C12M 1/04 | (2006.01) |
| C12M 1/12 | (2006.01) |

(Continued)

(52) U.S. Cl.
CPC ............. *C12N 13/00* (2013.01); *B82Y 25/00* (2013.01); *C12M 23/24* (2013.01); *C12M 23/50* (2013.01); *C12M 25/16* (2013.01); *C12N 5/0062* (2013.01); *H01F 1/0045* (2013.01); *H01F 7/0273* (2013.01)

(58) Field of Classification Search
CPC ....... B82Y 25/00; C12M 23/24; C12M 23/50; C12M 25/16; C12N 13/00; C12N 5/0062; H01F 1/0045; H01F 7/0273
USPC ................................ 435/289.1, 173.1, 284.1
See application file for complete search history.

(56) References Cited

U.S. PATENT DOCUMENTS

| 4,687,748 A | 8/1987 | Schroder |
|---|---|---|
| 4,897,444 A | 1/1990 | Brynes et al. |

(Continued)

FOREIGN PATENT DOCUMENTS

| CA | 1307225 | 9/1992 |
|---|---|---|
| CA | 1307225 C | 9/1992 |

(Continued)

OTHER PUBLICATIONS

U.S. Appl. No. 11/307,077, filed Jan. 23, 2006, Becker.

(Continued)

*Primary Examiner* — Nathan Bowers
(74) *Attorney, Agent, or Firm* — Wolf, Greenfield & Sacks, P.C.

(57) ABSTRACT

A culture apparatus and method for growing cells and tissue in a three-dimensional configuration harnesses magnetic, paramagnetic, ferromagnetic and diamagnetic forces. The cells or tissue are grown with magnetized core particles and are suspended via magnetic forces in a native, non-restricted, three-dimensional configuration while being maintained in a normal gravity (1 g) growth environment in the absence of rotational alteration of the gravity vector.

24 Claims, 6 Drawing Sheets

Related U.S. Application Data in-part of application No. 11/306,478, filed on Dec. 29, 2005, now abandoned, which is a continuation of application No. PCT/US2004/020908, filed on Jun. 30, 2004.

(60) Provisional application No. 60/481,042, filed on Jun. 30, 2003.

(51) Int. Cl.
*C12N 5/00* (2006.01)
*H01F 1/00* (2006.01)
*H01F 7/02* (2006.01)

(56) References Cited

U.S. PATENT DOCUMENTS

| | | | |
|---|---|---|---|
| 4,959,301 A | 9/1990 | Weaver et al. | |
| 4,988,623 A | 1/1991 | Schwarz et al. | |
| 4,994,388 A | 2/1991 | Hillegas et al. | |
| 5,026,650 A | 6/1991 | Schwarz et al. | |
| 5,100,799 A | 3/1992 | Mundt | |
| 5,153,131 A | 10/1992 | Wolf et al. | |
| 5,225,332 A | 7/1993 | Weaver et al. | |
| 5,269,745 A | 12/1993 | Liboff et al. | |
| 5,396,136 A | 3/1995 | Pelrine | |
| 5,427,935 A | 6/1995 | Wang et al. | |
| 5,458,558 A | 10/1995 | Liboff et al. | |
| 5,496,722 A | 3/1996 | Goodwin et al. | |
| 5,612,188 A | 3/1997 | Shuler et al. | |
| 5,935,849 A | 8/1999 | Schinstine et al. | |
| 5,989,913 A | 11/1999 | Anderson et al. | |
| 6,054,319 A | 4/2000 | Worden et al. | |
| 6,080,581 A | 6/2000 | Anderson et al. | |
| 6,203,487 B1 | 3/2001 | Consigny | |
| 6,326,203 B1 | 12/2001 | Worden et al. | |
| 6,383,470 B1 | 5/2002 | Fritzsch et al. | |
| 6,455,310 B1* | 9/2002 | Barbera-Guillem | 435/288.4 |
| 6,485,963 B1 | 11/2002 | Wolf et al. | |
| 6,673,597 B2 | 1/2004 | Wolf et al. | |
| 2002/0519850 | 7/2002 | El-Haj et al. | |
| 2002/0106314 A1* | 8/2002 | Pelrine et al. | 422/186 |
| 2002/0187721 A1* | 12/2002 | Chung | A63H 33/26 446/129 |
| 2003/0059764 A1 | 3/2003 | Ravkin et al. | |
| 2003/0077225 A1 | 4/2003 | Laurent et al. | |
| 2004/0058408 A1 | 3/2004 | Thomas et al. | |
| 2004/0208761 A1* | 10/2004 | Bader | C12M 29/10 417/417 |
| 2005/0101390 A1 | 2/2005 | Becker et al. | |
| 2005/0054101 A1 | 3/2005 | Felder et al. | |
| 2005/0255583 A1* | 11/2005 | DePaola | C12M 23/50 435/289.1 |
| 2006/0199170 A1 | 9/2006 | Becker | |
| 2009/0137018 A1 | 5/2009 | Becker et al. | |
| 2014/0087467 A1 | 3/2014 | Becker | |
| 2014/0356955 A1 | 12/2014 | Becker | |

FOREIGN PATENT DOCUMENTS

| | | |
|---|---|---|
| CN | 1289842 A | 4/2001 |
| WO | WO 82/00660 | 3/1982 |
| WO | WO 01/81460 A1 | 11/2001 |
| WO | WO 02/33419 | 4/2002 |
| WO | WO 02/51985 | 4/2002 |
| WO | WO 2005/003332 A2 | 1/2005 |
| WO | WO 2005/010139 | 2/2005 |

OTHER PUBLICATIONS

U.S. Appl. No. 14/090,655, filed Nov. 26, 2013, Becker.
U.S. Appl. No. 14/459,668, filed Aug. 14, 2014, Becker.
U.S. Appl. No. 12/330,071, filed Dec. 8, 2008, Becker et al.

[No Author Listed], Collagen from human placenta. Product No. C7521. Sigma-Aldrich. Updated May 2006. 1 page.
[No Author Listed], Phagocyte. Wikipedia. http://en.wikipedia.org/wiki/Phagocyte [last accessed Feb. 10, 2009]. 19 pages.
[No Author Listed], Rotate. Merriam-Webster Online. www.merriam-webster.com/dictionary/rotate [last accessed Feb. 10, 2009]. 2 pages.
[No Author Listed], Stir. Merriam-Webster Online. www.merriam-webster.com/dictionary/stir [last accessed Feb. 10, 2009]. 3 pages.
Dandagi et al., Mucoadhesive Microspheres of Propranodol Hydrochloride for Nasal Delivery. Indian J Pharm Sci. 2007;69(3):402-7.
Glogauer et al., A new method for application of force to cells via ferric oxide beads. Pflugers Arch. Jan. 1998;435(2):320-7.
Hammond et al., Optimized suspension culture: the rotating-wall vessel. Am J Physiol Renal Physiol. Jul. 2001;281(1):F12-25.
Knowles et al., Mechanism of collagen phagocytosis by human gingival fibroblasts: importance of collagen structure in cell recognition and internalization. J Cell Sci. Apr. 1991;98 ( Pt 4):551-8.
Krombach et al., Cell size of alveolar macrophages: an interspecies comparison, Environ Health Persepct. Sep. 1997;105 Suppl 5:1261-3.
Leach et al., Encapsulation of protein nanoparticles into uniform-sized microspheres formed in a spinning oil film. AAPS PharmSciTech. Dec. 6, 2005;6(4):E605-17.
Simon, M.D. et al. "Diamagnetically stabilized magnet levitation" *Am. J. Phys.*, 2001, 69(6):702-713.
Hopkin, M. "Magnet-making bacteria could target tumors" news@nature.com, retrieved Oct. 6, 2004.
"The Science 2009 Top 10 Innovations" 2009, pp. 1-9, www.the-scientist.com/article/print/56171.
Kato, K. et al. "Immobilized culture of nonadherent cells on an oleyl poly(ethylene glycol) ether-modified surface" *BioTechniques*, 2003, 35:1014-1021.
Kwon, Y.J. and Peng, C-A. "Calcium-alginate gel bead cross-linked with gelatin as microcarrier for anchorage-dependent cell culture" *BioTechniques*, 2002, 33:212-218.
Chang, AC and Gupta, RK, "Stabilization of Tetanus Toxoid in Poly(DL-lactic-co-glycolic acid) Microspheres for the Controlled Release of Antigen" *Pharmaceutical Sciences*, 1996, 85(2):129-132.
Carriere, D et al., "Whole Blood Capcellia CD4/CD8 Immunoassay for Enumeration of CD4+ and CD8+ Peripheral T. Lymphocytes" *Clinical Chemistry*, 1999, 45(1):92-97.
Levine, DW et al., "Optimization of Growth Surface Parameters in Microcarrier Cell Culture" *Biotechnology and Bioengineering*, 1979, 21(5):821-845.
Cartmell et al., "Preliminary analysis of magnetic particle techniques for activating mechanotransduction in bone cells" *IEEE*, 2002, p. 87-88.
Lo et al., "Cell-substrate separation: effect of applied force and temperature" *European Biophysics Journal*, 1998, p. 9-17.
Glogauer et al., "Magnetic fields applied to collagen-coated ferric oxide beads induce stretch-activated Ca flux in fibroblasts" *American Journal of Physiology of Cell*, 1995, p. C1093-C1104.
Schwarz et al., "Cell Culture for Three-Dimensional Modeling in Rotating-Wall Vessels: An Application of Simulated Microgravity" *J. Tiss. Cult. Meth.* 14, p. 51-58, 1992.
Simon et al., "Diamagnetically Stabilized Magnet Levitation" *American Association of Physics Teachers*, p. 702-713, 2001.
Altankov, G. et al. "Synthesis of protein-coated gelatin microspheres and their use as microcarriers for cell culture. Part I. Derivatization with native collagen" *J. Biomater. Sci. Polymer Edn.*, 1991, 2(2):81-89.
Emerich, D.F. and Winn, S.R. "Application of polymer-encapsulated cell therapy for CNS diseases" *Neuromethods*, 2000, 36:233-277.
Mathew, J. "A study of the fluid mechanics and the cultivation of mammalian cells in a magnetically stabilized fluidized bed bioreactor" Thesis submitted Aug. 1994 at Rice University, UMI Microform No. 9715030, copyright 1997, pp. 1-166.

(56) References Cited

OTHER PUBLICATIONS

Nallapareddy, S. et al. "*Enterococcus faecalis* adhesion, ace, mediates attachment to extracellular matrix proteins collagen type IV and laminin as well as collagen type I" *Infect. Immun.*, 2000, 68(9):5218-5224.

Suh, H. et al. "Regulation of smooth muscle cell proliferation using paclitaxel-loaded poly(ethylene oxide)-poly(lactide/glycolide) nanospheres" *J. Biomed. Mater. Res.*, 1998, 42:331-338.

International Search Report and Written Opinion mailed Jul. 1, 2005 for Application No. PCT/US2004/020908.

International Preliminary Report on Patentability mailed Jan. 3, 2006 for Application No. PCT/US2004/020908.

[No Author Listed], Diamagnetic Levitation. www.physics.ucla.edu/marty/diamag/index.html [last accessed Oct. 24, 2014]. 3 pages.

[No Author Listed], Diamagnetically stabilised levitation. Aug. 16, 1999. XP002331831. http://www.hfml.ru.nl/fingertip.html [last accessed Dec. 5, 2014]. 2 pages.

[No Author Listed], Microarray. Dec. 8, 1998. http://www.tmc.tulane.edu/astrobiology/microarray/default.html_1998. [last accessed Mar. 29, 2006]. 2 pages.

[No Author Listed], Welcome to the Larry the Frog Magnetic Levitation Movie Theater . . . May 12, 2001. http://pub26.bravenet.com/forum/static/show.php?usernum=2207974340&frmid=3071&msgid=104756&cmd=show [last accessed Dec. 2, 2014]. 3 pages.

Becker et at, Three-Dimensional Growth and Differentiation of Ovarian Tumor Cell Line in High Aspect Rotating-Wall Vessel: Morphologic and Embryologic Considerations. J Cell Biochem. 1993;51:283-9.

Carmeliet et al., Microgravity Reduces the Differentiation of Human Osteoblastic MG-63 Cells. National Library of Medicine. J Bone Miner Res. May 1997;12(5):786-94.

Database WPI, AN 2001-390726. Class D16. Section Ch, Week 200142. Derwent Publications Ltd., London, GB. Apr 4, 2001. 4 pages.

Geim et al., Magnet levitation at Your Fingertips. Nature. Jul. 22, 1999;400:323-4.

Geim, Everyone's Magnetism. Physics Today. Sep. 1998:36-9.

Goodwin et al., Three-Dimensional Culture of a Mixed Mullerian Tumor of the Ovary: Expression of In Vivo Characteristics. In Vitro Cell Dev Biol—Animal. May 1997;33:366-74.

Hammond et al., Mechanical Culture Conditions Effect Gene Expression; Gravity-Induced Changes on the Space Shuttle. Physiol Genomics. 2000;3(3):163-73. Epub Sep. 8, 2000. 15 pages.

HFML University of Nijmegen, Levitation. www.hfml.kun.nl/fingertip.html [last accessed Mar. 29, 2006]. 2 pages.

HFML University of Nijmegen, The Real Levitation. www.hfml.sci.kun.nl/levitate.html [last accessed Apr. 7, 2003]. 2 pages.

Johanson et al. *Saccharomyces* Cerevisiae Gen Expression Changes During Rotating Wall Vessel Suspension Culture. J Appl Physiol. 2002;93:2171-80.

Lewis et al., cDNA Microarray Reveals Altered Cytosleletal Gene Expression in Space-Flown Leukemic T Lymphocytes (Jurkat). FASEB J. Aug. 2001;15:1783-5.

Prewett et al., Three-Dimensional Modeling of T-24 Human Bladder Carcinoma Cell Line: A New Simulated Microgravity Culture Vessel. J Tiss Cult Meth. 1993;15:29-36.

Simon et al., Diamagnetic Levitation: Flying Frogs and Floating Magnets. J Appl Phys. May 1, 2000;87(9):6200-4.

Tsao et al., Responses of Gravity Level Variations on the NASA/JSC Bioreactor System. Physiologist. 1992;35(1):549-50.

U.S. Appl. No. 11/306,478, filed Dec. 29, 2005, Abandoned.

\* cited by examiner

MAGNETIC THREE-DIMENSIONAL CELL CULTURE APPARATUS AND METHOD

CROSS-REFERENCE TO RELATED APPLICATIONS

The present application is a divisional of U.S. application Ser. No. 12/330,071, filed Dec. 8, 2008, which is a continuation-in-part of U.S. application Ser. No. 11/306,478, filed Dec. 29, 2005, which is a continuation of International Application No. PCT/US2004/020908, filed Jun. 30, 2004, which claims the benefit of U.S. Provisional Application Ser. No. 60/481,042, filed Jun. 30, 2003.

BACKGROUND OF THE INVENTION

1. Field of the Invention

This invention relates, generally, to the fields of biophysics, tissue regeneration, tissue culture and neurobiology. More particularly, it relates to a method and apparatus for potentiation of or controlling the growth of biological cells and tissue in vitro.

2. Description of the Prior Art

Conventional cell culturing involves placing a small number of cells into a nutrient-rich media, typically a petri dish or flask, and allowing the cells to grow and multiply. The result is a two dimensional growth of cells. This provides limited insight as to how the cells would actually grow and multiply in three dimensions, i.e., in vivo. Without a proper three-dimensional assembly, epithelial and mesenchymal cells, which are the basic cells that differentiate tissue into specific organ functions, lack the proper indicators for growing into a variety of cells that make up a specific tissue. It is known that cells self-associate in the body, i.e., replication involves association with the proper connections in the surrounding environment, as in the body, for proper growth clues to naturally form. It is therefore desirable to have a culture environment that simulates tissue assembly in the body to provide the proper growth clues to the cells.

Systems are known that attempt to provide a three-dimensional cell culture environment. The bioreactor developed by NASA in the 1980s is one such system. The bioreactor is a can-like rotating vessel with a membrane for gas exchange that allows nutrients in and carbon dioxide and wastes out. As the bioreactor turns, the cells continually fall through the medium yet never hit bottom, thus promoting self-association in a proper growth environment. As such, the cells form clusters and grow and differentiate as they would in the body. This culture environment is referred to as simulated or modeled microgravity.

The desire to provide three-dimensional cell cultures has led others to the use of time varying electromagnetic fields and other mechanical devices to help grow and orient three-dimensional tissue in vitro.

WO 02/051985 teaches a method of culturing cells in a bioreactor that supplies a continuous supply of culture medium. Magnetic material in the form of micro or nano particles is attached to the tissue forming cells. The cells are then subjected to a magnetic field that varies sinusoidally at a frequency between 0.1-10.0 Hz. The resulting mechanical stresses are applied to the cells and the result of such mechanical stress is tissue growth. More particularly, the invention provides a method for culture while subjecting tissue or cells to repeatedly applied magnetically-generated mechanical stresses and the result of such mechanical stress is tissue or cell growth. The stresses may be administered via a magnetic material attached to the cells such as micro or nano particles, or may be a magnetic material that is inserted into the culture medium as a ferrofluid.

Simon et al. in the Journal of Applied Physics (2000) and in the American Journal of Physics (June 2001) disclose levitation of living things such as frogs using permanent magnets and diamagnetic plates. No cell culture is positioned in the magnetic field between the permanent magnets and the diamagnetic plates. None of the cells that collectively form the frog are changed when the frog is released from the magnetic field.

U.S. Pat. No. 5,396,136 to Pelrine discloses a two dimensional array of permanent magnets levitated over a layer of pyrolytic graphite, a diamagnetic material. No cell culture is positioned in the magnetic field between the permanent magnets and the diamagnetic plate. The levitation of permanent inanimate magnets has potential utility in connection with magnetic levitation trains or in instruments such as accelerometers or gyroscopes.

U.S. Pat. No. 6,203,487 to Consigny discloses microspheres that are incorporated into cells. The microspheres have a diameter of about four and one-half microns (4.5 µm) and are guided by magnets to a target tissue such as blood vessels damaged during a surgical procedure. Three dimensional cell growth is not disclosed by Consigny nor would such cell growth be likely in view of the very small size of the microspheres. In balloon angioplasty where artery-clogging plaque is removed, it is desirable to deliver single cells to the damaged artery by following the Consigny teachings but it would be undesirable to deliver an artery-clogging three dimensional mass of cells to such a location. Therefore it may be concluded that the Consigny teachings do not include the formation of three dimensional cell growth.

It is desirable to provide a realistic environment and in vivo-like growth conditions to develop in vitro models of cell and tissue biology and functionality that replicate the conditions in the body in which the cells and tissue normally grow. However, the systems and methods currently known in the art do not provide this desirable realistic environment. The simulation of microgravity associated with the continuous rotation of a culture chamber creates a problem associated with the alteration of genes and thus protein expression due to the constant randomization of the gravity vector attributed to the continuous rotation.

It would also be desirable to provide a system that does not require electrically conductive channels, thereby eliminating the need for a constant supply of electricity.

There remains a need, therefore, for a system and method to provide a realistic environment for developing in vitro models of cell and tissue biology and functionality that replicate the conditions in the body in which the cells and tissue normally grow.

However, in view of the prior art considered as a whole at the time the present invention was made, it was not obvious to those of ordinary skill in the pertinent art how the identified need could be fulfilled.

BRIEF SUMMARY OF THE INVENTION

The longstanding but heretofore unfulfilled need for a system and method to provide an environment from which to develop three dimensional in vitro models of cell and tissue biology and functionality that replicate the conditions in the body in which the cells and tissue normally grow is now met by a new, useful, and nonobvious invention without utilizing rotation or electromagnetic fields.

The present invention is a culture apparatus and method for growing cells, tissue, or cells and tissue in a three-dimensional configuration using magnetic, paramagnetic, ferromagnetic and diamagnetic forces, alone or in combination. The cells/tissue are grown within the novel culture apparatus on magnetized core particles and are suspended via magnetic forces in a native, non-restricted, three-dimensional configuration while being maintained in an earth gravity (1 g) growth environment. This eliminates the rotational alteration of the gravity vector that characterizes prior art techniques.

The present invention purposely does not subject cells/tissue to mechanical stressors. It is a method for quiescent tissue culture conducted specifically in the absence of such stressors.

The cellular constructs generated in the culture device of the present invention can be utilized for applications including, but not limited to, pharmacological testing and development of new types of biologic and therapeutic agents, cellular factor/protein production, generation of tissue for transplant to replace damaged tissue, and development of functional three-dimensional cellular constructs for biosensing activities.

The system and method of the invention are utilized in combination with known tissue culture processes to produce enhanced three-dimensionally directed cell growth and tissue formation organization.

A first embodiment includes an upper lifter magnet, stabilizing diamagnets, and a culture chamber containing a culture medium and a plurality of bioattractive magnetized core particles. The culture chamber is positioned relative to the upper lifter magnet and diamagnets to facilitate levitation of the magnetized core particles.

A variety of diamagnets are within the scope of the invention. A single magnet in the form of a toroid may supply the diamagnetic force. However, two diamagnetic plates may supply the diamagnetic force, with the culture chamber being positioned substantially between the two plates. The system may also include a plurality of diamagnets positioned to provide the diamagnetic force for levitation of the magnetized core particles.

The novel culture chamber contains a culture medium and a plurality of bioattractive magnetized core particles. As biological cells to be cultivated are introduced into the culture chamber, they adhere to the bioattractive magnetized core particles. The subsequent growth of the cells provides a three-dimensional cellular construct. The novel culture chamber may be gas permeable to enable the exchange of oxygen, carbon dioxide and other gases through the chamber. Additionally, the culture chamber may include an influx port allowing the introduction of new culture media into the chamber and an outflux port to enable removal of spent culture media.

The magnetized core particles within the culture chamber are preferably coated with a cellular adhesive material such as a collagen or other matrix component to facilitate cellular adherence and three-dimensional growth. The matrix components may be biodegradable or non-biodegradable. Other methods and materials designed to encourage cellular adhesion to the magnetized core particles are within the scope of the invention. Moreover, the magnetized core particles may be shaped to achieve a predetermined cellular construct shape, such as that of skin or other tissue.

The upper lifter magnet can also be used as a removal magnet to remove the magnetized core particles subsequent to a predetermined culture cultivation period. As such, the magnetized core particles can be dissociated from the cellular aggregates by adherence to the removal magnet at the termination of the culture period.

The method steps include inoculating a plurality of biological cells into a culture chamber containing a culture medium and a plurality of bioattractive magnetized core particles, thereby initiating the adherence of the biological cells to the magnetized core particles. The culture chamber is positioned relative to the upper lifter magnet and the diamagnets to facilitate levitation of the magnetized core particles, and cell growth is monitored.

In another embodiment, the novel method includes the steps of introducing new culture media into the culture chamber through an influx port and removing spent culture media from the culture chamber through an outflux port.

In yet another embodiment, at a desired termination of the culture period, the magnetized core particles are removed from the culture chamber by positioning the upper lifter magnet in a predetermined position relative to the culture chamber, and using the upper lifter magnet effectively in the removal of the magnetized core particles.

Accordingly, the present invention provides a solution to in vitro three-dimensional suspension culture of cells under quiescent growth conditions characterized by zero shear and turbulence while maintaining a 1 g, normal gravity environment as distinguished from a simulated microgravity environment. This facilitates cellular co-localization and three-dimensional aggregate formation akin to an in vivo configuration.

The present invention provides many advantages over conventional systems and methods for three-dimensional cell growth, including a more realistic and in vivo-like growth condition from which to develop in vitro models of cell and tissue biology and functionality that replicate the conditions in the body within which the cells/tissue normally grow.

The present invention also eliminates problems associated with altering gene, and thus protein, expression by conventional means of simulated microgravity associated with continuous rotation of the culture chamber that produces constant randomization of the gravity vector.

The present invention also provides an apparatus and method affording these advantages in a three-dimensional culture that does not require electrically conductive channels to create electromagnetic fields or waveforms.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE INVENTION

In accordance with a first embodiment, a novel apparatus includes an in vitro culture device utilizing magnetic, paramagnetic, ferromagnetic and diamagnetic fields to create a suspension culture in which to grow cells, tissue, or both. The novel culture chamber may be formed of a plastic or plastic-like material that is preferably gas permeable. Cells are grown in the novel culture chamber as three-dimensional tissue-like aggregate constructs under conditions of zero shear and turbulence, and in a normal gravity (1 g) environment.

Figure 1:
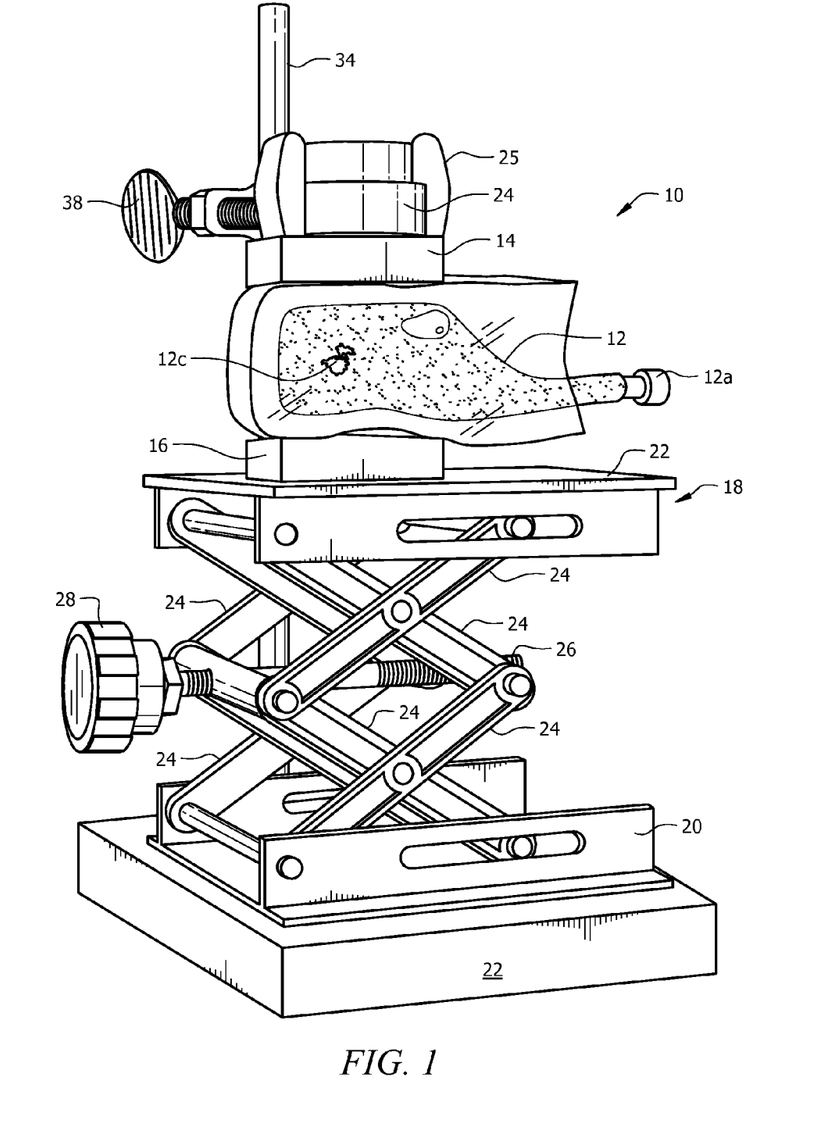
FIG. 1 is a perspective view of the novel magnetic culture device setup demonstrating levitation of magnetic microcarriers within a culture bag.

Referring now to FIG. 1, it will there be seen that an illustrative embodiment of the invention is denoted as a whole by the reference numeral 10.

FIG. 1 depicts a first embodiment. Culture bag or chamber 12 is positioned in sandwiched relation between two stabilizing diamagnetic plates 14, 16.

The plates are supported by lab-jack 18 that is well-known and commercially available from many sources. Lab jack 18 includes base 20, platform 22, a plurality of pivotally interconnected links collectively denoted 24, and a screw 26 having a thumb-turn head 28 to facilitate manual advancement or retraction of the screw. Such advancement or retraction causes pivoting of the links about their respective pivot points and thereby adjusts the height of platform 22 relative to base 20. Base 20 is supported by a table top or incubator shelf 22. Lab jack 18 provides a stable, height-adjustable support surface to facilitate levitation of the three-dimensional construct in the center of the culture bag or chamber.

Lab jack 18 is adjusted to the height at which the 3D construct levitates in the center of culture chamber 12, as determined by visual observation.

Culture bag or chamber 12 contains magnetized core particles, culture medium and biological cells to be cultivated. The three-dimensional cellular constructs are adhered to magnetized core particles and are held in suspension in the magnetic field provided by upper lifter magnet 24 and said magnetic field is stabilized by repelling forces supplied by diamagnets 14, 16, which may be provided as two single or several small diamagnets distributed over a surface.

Figure 2:
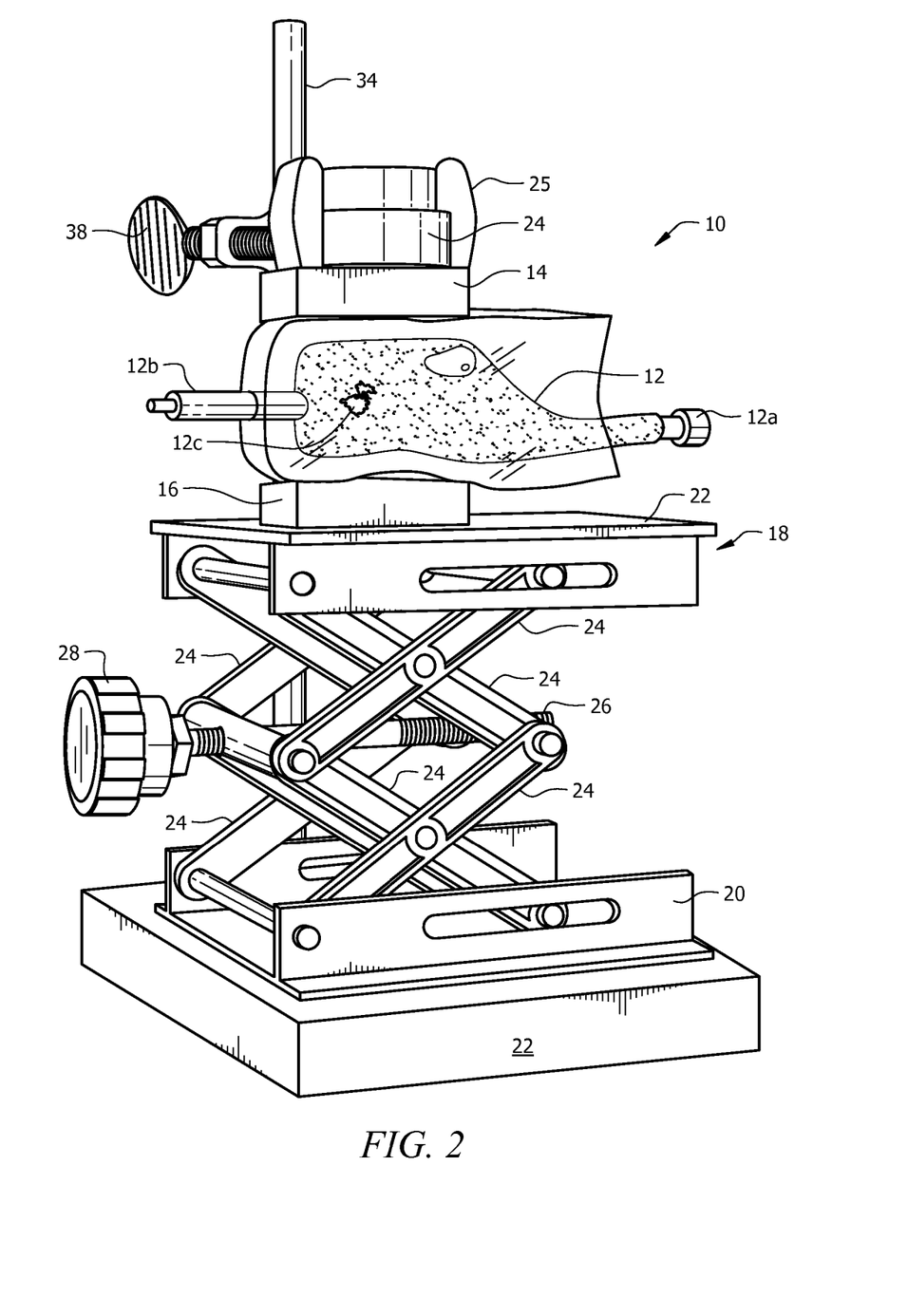
FIG. 2 is a perspective view of an embodiment of the novel magnetic culture device that includes a culture bag having influx and outflux ports.

The novel magnetic cell culture device preferably includes a culture media flow-through system so that new media is slowly infused into the vessel and a substantially equal amount of spent culture is removed at the same time. In the embodiment of FIG. 2, the flow through system includes inlet port 12a on a first end of the magnetic cell culture device, and outlet port 12b on a second end substantially opposite the inlet port. Inlet port 12a may serve as a luer lock or closed cap or it may be modified to serve as an inlet port. Other configurations of the inlet and outlet ports are within the scope of this invention. The culture media flow through the novel apparatus is adapted to be attached to a supply of fresh media, while spent media is collected in a reservoir for subsequent removal. The spent media may be further purified to provide purified cell-produced factors and proteins derived from the growing three-dimensional cellular constructs.

In a preferred embodiment, the strength of lifter magnet 24 is between one to two tesla (1-2 T).

Magnet 24 is used to "dredge" or slide over culture bag 12 to separate out the magnetized core particles and draw them to one side for removal through the port. In the alternative, culture bag 12 could be cut open and the contents placed into a dish for subsequent core particle removal in a similar fashion, i.e., sliding over the magnet as stated above to segregate the particles.

Figure 3:
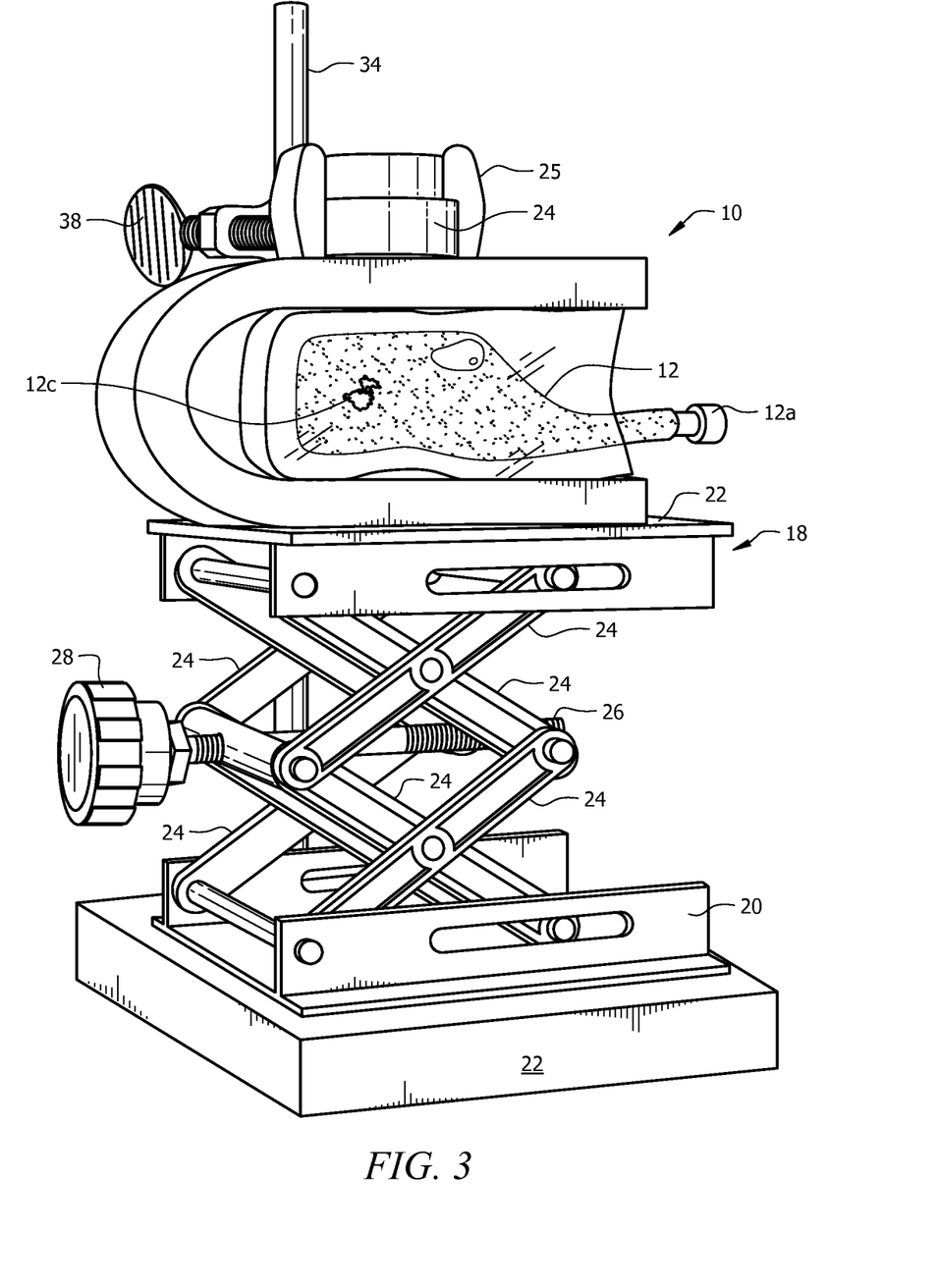
FIG. 3 is a perspective view of an embodiment having a single "U"-shaped diamagnet.

As depicted in FIG. 3, a single diamagnet such as a "U"-shaped diamagnet 30 may supplant diamagnets 14, 16.

Figure 4:
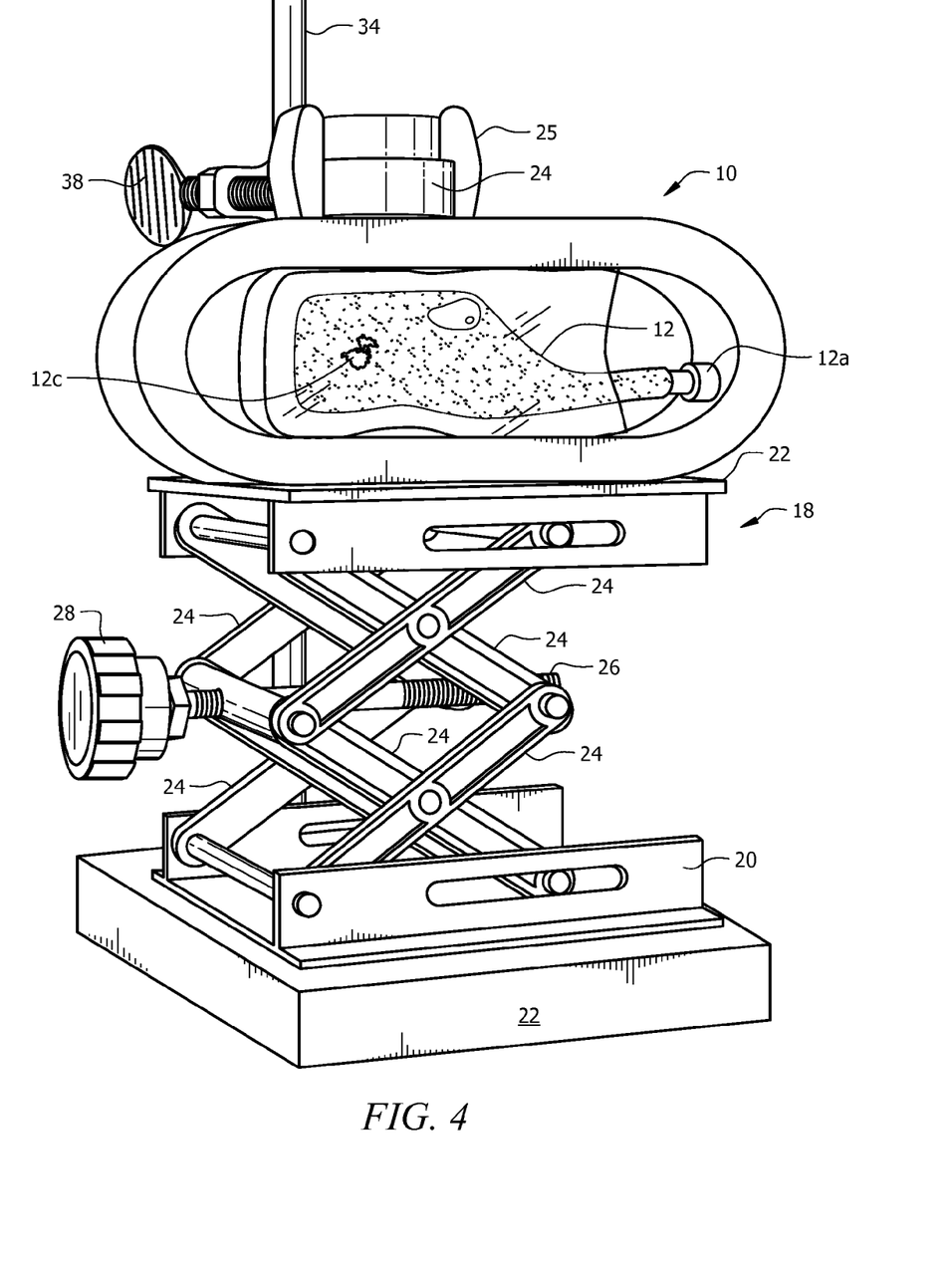
FIG. 4 is a perspective view of an embodiment having a single toroidal-shaped diamagnet.

Moreover, a single diamagnet such as toroidal diamagnet 32 as depicted in FIG. 4 may also supplant said diamagnets 14, 16.

Figure 5:
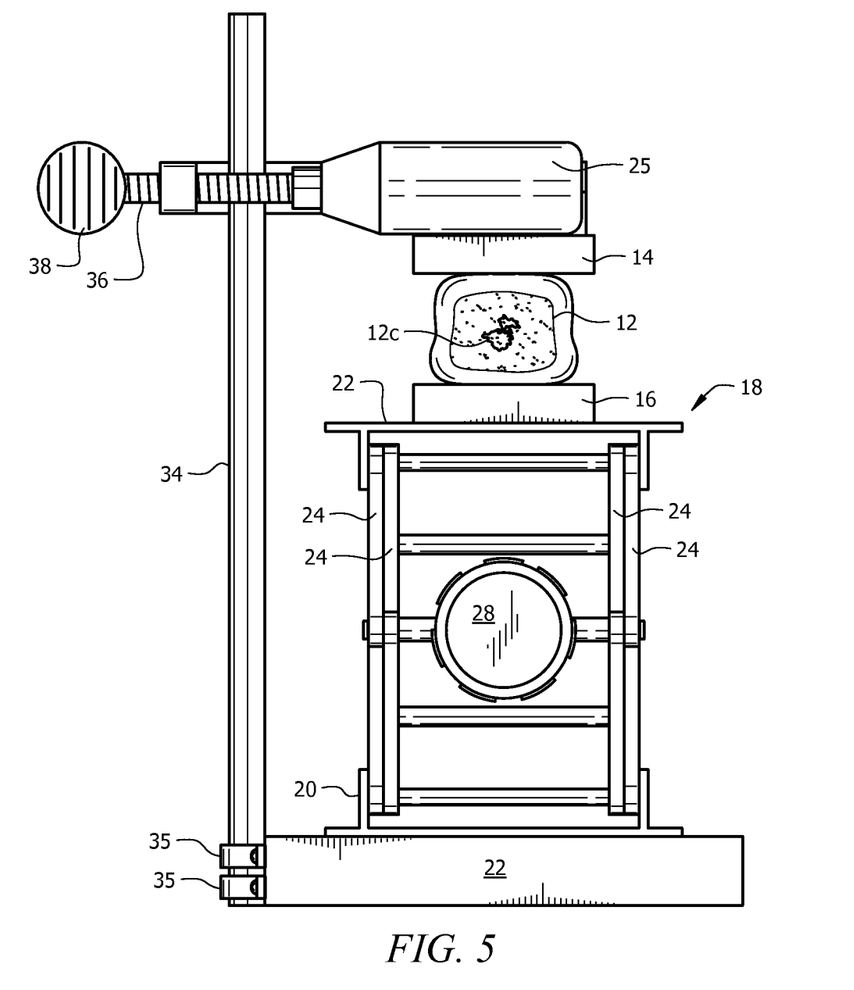
FIG. 5 is an end view of the embodiment of FIG. 1.
Figure 6:
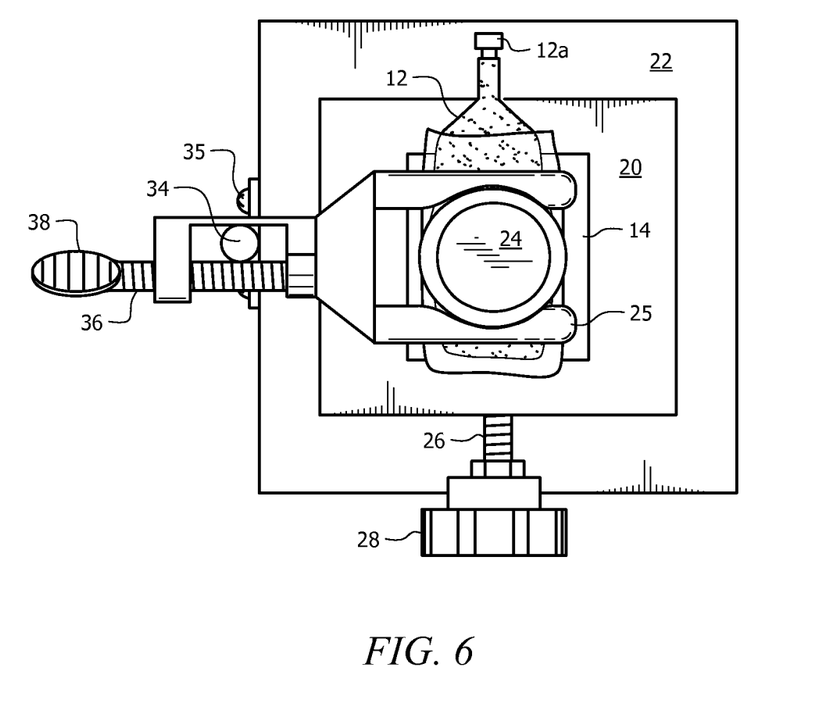
FIG. 6 is a top plan view of the embodiment of FIG. 1.

FIG. 5 depicts the embodiment of FIG. 1 in end elevation and FIG. 6 depicts said embodiment in top plan view.

Cells are grown on magnetized core particles, also known as microcarriers, within the magnetic cell culture device. The magnetized core particles are coated with cellular adhesive material such as collagen and other matrix components to facilitate cellular adherence and three-dimensional growth.

The microcarriers are ferromagnetic, i.e. they are not inherently magnetic but become magnetized upon exposure to a magnetic field. Accordingly, they are easy to prepare prior to magnetization because they do not adhere to one another until they are put into the magnetic field, i.e., until they are placed into the culture bag between diamagnets 14, 16 under the influence of lifter magnet 24. However, the invention also works well using regular magnetic microcarriers. The magnetic core particles function as desired because the magnetic field is provided by the influence of upper lifter magnet 24.

The field strength inside culture bag 12, i.e., within the culture fluid, is preferably less than sixty gauss (60 G).

The coating is applied during an incubation procedure as disclosed in the co-pending disclosure referred to below.

In the case of growing cells adhered to magnetized core particles, the matrix material on such particles may be non-degradable by the cells that are growing on said material or may be biodegradable such that growing cellular aggregates actually degrade the matrix as cell growth continues so that the cells in three dimensional constructs fall away from the core particles after a significant period of time in culture.

In the case of core particles coated with a non-degradable matrix, the cellular constructs at the termination of the culture period are dispersed from the magnetized core particles by well-known enzymatic digestion techniques and the magnetized core particles upon which there are no cellular constructs are eliminated from the dissociated cellular aggregates by adherence to magnet 24.

The magnetized core particles may be shaped to specific dimensions to achieve desired cellular construct shapes. For example, they may be shaped in molds to make replacement bone joints and cartilage. As another example, cellular construct shapes are created for specified sized and shaped pieces of skin, or any other type of organ-specific tissue. The uses for such shapes include but are not limited to pharmacological testing of new types of biologic and therapeutic agents and for transplants to replace damaged tissue. The magnetic cell culture device may be utilized to enhance specific cellular geometries associated with particular biological functions, including but not limited to drug uptake, transport and metabolism, cellular factor/protein production, and bio-sensing activities.

Provided is a microcarrier bead having a supporting surface for the attachment of cells, the microcarrier bead further comprising, at least one magnetically charged molecule and a cellular matrix material. In one embodiment the magnetically charged molecule is magnetite ($Fe_3O_4$) and the microcarrier cellular matrix material is Type I solubilized collagen. The support material may be constructed from porous gelatin.

Additional disclosure that may be required to enable those of ordinary skill to make and use this invention without undue experimentation is provided in co-pending patent application bearing Ser. No. 11/307,077, filed Jan. 23, 2006 by the same inventor, entitled "Ferromagnetic Cell and Tissue Culture Microcarriers." That co-pending disclosure is hereby incorporated by reference in its entirety into this disclosure.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. An apparatus comprising:
a cell culture chamber;
a plurality of magnetized core particles contained within the cell culture chamber;
a magnet operatively coupled to the cell culture chamber, wherein the magnet is configured to be selectively moved between at least a first position and a second position relative to the cell culture chamber, and wherein movement of the magnet between the first position and the second position relative to the cell culture chamber changes a strength of the magnetic field present within the cell culture chamber to control levitation of the plurality of magnetized core particles located within the cell culture chamber, wherein the magnet is capable of movement during a cell culture process; and
a first diamagnet and a second diamagnet, wherein the cell culture chamber is positioned between a first diamagnet and a second diamagnet such that the plurality of magnetized core particles are levitated between the first diamagnet and the second diamagnet.

2. The apparatus of claim 1, wherein said cell culture chamber contains a cell culture medium.

3. The apparatus of claim 2, wherein said cell culture chamber includes biological cells to be cultivated.

4. The apparatus of claim 1, wherein said cell culture chamber is formed of a gas permeable material.

5. The apparatus of claim 1, further comprising:
an inlet port formed in said cell culture chamber at a first end of said cell culture chamber; and
an outlet port formed in said cell culture chamber at a second end of said cell culture chamber, said second end being spaced apart from said first end.

6. The apparatus of claim 2, wherein said magnetized core particles are coated with a cellular adhesive material.

7. The apparatus of claim 2, wherein said magnetized core particles are coated with a collagen component.

8. The apparatus of claim 2, wherein said magnetized core particles are coated with a matrix component.

9. The apparatus of claim 8, wherein said matrix component is non-biodegradable.

10. The apparatus of claim 8, wherein said matrix component is biodegradable.

11. The apparatus of claim 1, wherein said magnetized core particles are adapted to form a predetermined cellular construction.

12. The apparatus of claim 11, wherein said predetermined cellular construction is mammalian skin.

13. The apparatus of claim 11, wherein said predetermined cellular construction is a mammalian organ.

14. The apparatus of claim 11, wherein said predetermined cellular construction is mammalian tissue.

15. The apparatus of claim 2, wherein a plurality of cells are adhered to and growing on said magnetized core particles in a three-dimensional configuration.

16. The apparatus of claim 1, wherein a strength of said magnet is one to two tesla.

17. The apparatus of claim 1, wherein a field strength inside said cell culture chamber is less than 60 gauss.

18. The apparatus of claim 2, wherein said magnetized core particles are ferromagnetic.

19. The apparatus of claim 1, wherein the first diamagnet and the second diamagnet are opposing portions of a "U"-shaped diamagnet.

20. The apparatus of claim 1, wherein the first diamagnet and the second diamagnet are opposing portions of a toroidal diamagnet.

21. The apparatus of claim 1, wherein the magnet applies a magnetic force to levitate the plurality of magnetized core particles in the first position.

22. The apparatus of claim 1, wherein the magnet applies a magnetic force to draw the plurality of magnetized core particles to one side of the cell culture chamber in the second position.

23. The apparatus of claim 1, wherein the magnet is disposed in abutting relation to the first diamagnet.

24. The apparatus of claim 1, further comprising an opening to the cell culture chamber consisting of an inlet port formed in said cell culture chamber.

* * * * *